United States Patent
Langois et al.

(10) Patent No.: US 9,759,687 B2
(45) Date of Patent: Sep. 12, 2017

(54) METHOD AND A DEVICE FOR DETECTING DEFECTS IN A PACKAGING MATERIAL

(75) Inventors: Philippe Langois, Sollentuna (SE); Hans Hallstadius, Lund (SE)

(73) Assignee: TETRA LAVAL HOLDINGS & FINANCE S.A., Pully (CH)

( * ) Notice: Subject to any disclaimer, the term of this patent is extended or adjusted under 35 U.S.C. 154(b) by 92 days.

(21) Appl. No.: 13/977,451

(22) PCT Filed: Dec. 22, 2011

(86) PCT No.: PCT/SE2011/051574
§ 371 (c)(1),
(2), (4) Date: Jun. 28, 2013

(87) PCT Pub. No.: WO2012/091661
PCT Pub. Date: Jul. 5, 2012

(65) Prior Publication Data
US 2014/0009169 A1   Jan. 9, 2014

(30) Foreign Application Priority Data

Dec. 29, 2010 (SE) .................................. 1001233
Dec. 29, 2010 (SE) .................................. 1001235

(51) Int. Cl.
*G01N 27/92* (2006.01)
*G01M 3/40* (2006.01)
*G01R 31/12* (2006.01)

(52) U.S. Cl.
CPC .............. *G01N 27/92* (2013.01); *G01M 3/40* (2013.01); *G01R 31/1227* (2013.01)

(58) Field of Classification Search
CPC ................................ G01M 3/40; G01N 27/205
See application file for complete search history.

(56) References Cited

U.S. PATENT DOCUMENTS

| 4,914,395 | A  | * | 4/1990 | Hamada | ................. | G01M 3/40 |
| | | | | | | 324/514 |
| 6,593,752 | B1 | * | 7/2003 | Yasumoto | ..................... | 324/557 |
| 6,794,885 | B1 | * | 9/2004 | Yasumoto | ..................... | 324/557 |
| 7,015,700 | B2 | * | 3/2006 | Konno et al. | ................. | 324/444 |

(Continued)

FOREIGN PATENT DOCUMENTS

| CN | 1350639 | 5/2002 |
| EP | 1 167 956 A1 | 1/2002 |

(Continued)

OTHER PUBLICATIONS

Translation of JP2004-069458.*
International Search Report of PCT/SE2011/051574 mailed on Apr. 2, 2013, 3 pages.
Japanese Office Action mailed Jul. 15, 2016, by the Japanese Patent Office in counterpart Japanese Patent Application No. 2013-547402.

*Primary Examiner* — Huy Q Phan
*Assistant Examiner* — Adam Clarke
(74) *Attorney, Agent, or Firm* — Finnegan, Henderson, Farabow, Garrett & Dunner LLP

(57) ABSTRACT

A method and a device for detecting defects in a packaging laminate having at least one conductive layer are provided. The method comprises the steps of grounding the conductive layer of the packaging laminate, arranging an electrode adjacent to the packaging laminate, applying a high voltage to the electrode by ramping the voltage from an initial value towards an upper predetermined value, and detecting a defect in the packaging material by registering dielectric breakdown between the electrode and the conductive layer of the packaging laminate.

16 Claims, 5 Drawing Sheets

(56) References Cited

U.S. PATENT DOCUMENTS

| | | | |
|---|---|---|---|
| 2003/0062919 A1* | 4/2003 | Vargas | 324/766 |
| 2005/0151529 A1* | 7/2005 | Ishida | B29C 65/7451 |
| | | | 324/71.1 |
| 2007/0128759 A1* | 6/2007 | Dewes | B81C 99/0045 |
| | | | 438/53 |
| 2009/0165536 A1* | 7/2009 | Kinoshita | 73/52 |
| 2010/0117676 A1* | 5/2010 | Yiang | G01R 31/318511 |
| | | | 324/762.05 |
| 2012/0068716 A1* | 3/2012 | Reed | G01N 27/61 |
| | | | 324/454 |

FOREIGN PATENT DOCUMENTS

| | | |
|---|---|---|
| EP | 1 965 207 A1 | 9/2008 |
| JP | S59-125035 | 7/1984 |
| JP | 8240569 A | 9/1996 |
| JP | EP 1022106 A1 * 7/2000 | ............ B29D 7/01 |
| JP | 2000-258399 | 9/2000 |
| JP | 2004069458 A | 3/2004 |
| JP | 2007-170893 | 7/2007 |
| SU | 1056027 A | 11/1983 |
| SU | 1760478 | 9/1992 |
| WO | WO 99/08853 | 2/1999 |

\* cited by examiner

METHOD AND A DEVICE FOR DETECTING DEFECTS IN A PACKAGING MATERIAL

CROSS-REFERENCE TO RELATED APPLICATIONS

This is a U.S. National Phase of PCT/SE2011/051574, filed Dec. 22, 2011, which claims the benefit of priority to Swedish Patent Application Nos. 1001233-4, filed Dec. 29, 2010 and 1001235-9, filed Dec. 29, 2010, which are incorporated herein by reference.

TECHNICAL FIELD

The present invention relates to a method and a device using high voltage for detecting defects in a packaging laminate.

BACKGROUND

Packaging laminates are used for enclosing food products, especially liquid food such as drinks and other beverages. A typical laminate consists of a core layer of paper based material being covered on one side by a thermoplastic polymer layer facing the outer environment of the package to be formed. The inside of the packaging laminate may comprise a multi-layer structure, including a first layer of polymer being in contact with the core layer, a barrier film of Al, and subsequent polymer layers to be in contact with the enclosed product.

In certain applications the packaging laminate may be provided with pre-laminated holes, i.e. areas where the core layer is removed such that the outer thermoplastic polymer layer is in direct contact with the inside multi-layer laminate structure. Such pre-laminated holes may e.g. be provided for facilitating the arrangement of opening devices such as re-closeable caps, or as straw holes. By removing the core layer of paper based material at the position of the pre-laminated holes, easy opening of an opening device arranged at the position of the pre-laminated hole is enabled.

Generally, the position of the pre-laminated hole is determined by punching the core layer before lamination.

During the provision of pre-laminated holes different failure modes may occur. For example, air may be trapped between the Al foil and the inside polymer film. The presence of such air inclusions may cause cracks or open holes in the polymeric layers during lamination, and it will thus affect the aseptic performance of the package. Another example is the formation of pinholes, which may occur during extrusion coating of the polymeric layers. Since the aseptic performance of the packaging laminate is critical, it is desired to have a method for detecting such defects.

One such method relies on the operation of a conductivity meter. In this method, the surface of the pre-laminated hole is provided with a thin film of electrolyte, e.g. $NH_4Cl$ at a concentration of 20 g per liter water. The Al foil is connected to a low voltage electrode, and a second electrode, having a planar surface of approximately 3 mm in diameter, is moved in close contact over the pre-laminated hole. When applying a low voltage to the electrodes, in combination with a high resistance in series with the test circuit and a signal amplifier, pin holes creating a contact and thus a closed circuit are easily detected.

Another system presently on the market uses a high voltage roller electrode that continuously passes over a grounded substrate. A spark over is created and registered when the electrode passes over a defective spot.

Although this known system may be suitable for some applications, it may not be used in an advantageous way to register defects of a pre-laminated hole, since the topography is disruptive at the edges of such holes. This means that the roller electrode will loose contact with the pre-laminated hole and consequently it will have an inconsistent sensitivity for any defects on this area. Moreover, the known system requires a dry sample since water on the surface will create a short circuit on the sample.

BRIEF SUMMARY

An object of the present invention is to reduce or eliminate the above-mentioned drawbacks.

An object is to provide a method and a device for detecting defects on a substrate having a disruptive topography.

An object is to provide a method and a device having a sufficient resolution for detecting sub-mm defects on lowered areas of a packaging laminate, such as a pre-laminated hole.

It is within the scope of the present invention to provide a method and a device being capable of determining not only the presence of defects, but also details of said defects; and/or It is within the scope of the present invention is to provide a method and a device being capable of providing continuous results of defect presence during a detecting sequence.

Determination of the defects can be in a non-contact mode, i.e. the electrode is at a predetermined distance from the packaging material.

According to one aspect of the invention, a method for detecting defects in a packaging laminate having at least one conductive layer is provided. The method comprises the steps of grounding the conductive layer of the packaging laminate, arranging an electrode adjacent, optionally at a pre-determined distance, to said packaging laminate, applying a high voltage to said electrode optionally by ramping the voltage from an initial value towards an upper value, optionally a predetermined value, and detecting a defect in said packaging material by registering dielectric breakdown between the electrode and the conductive layer of the packaging laminate.

Generally defects are pinholes and/or weaknesses in the packaging laminate.

The step of arranging the electrode may comprise bringing the electrode in close contact with a predefined area of said packaging laminate, which is advantageous in that further parameters of the packaging laminate, such as polymer layer thickness, may be determined.

According to the invention the determination can be made in a non-contact mode or where the electrode may be in direct contact with the packaging laminate. The non-contact generally refers to arranging the electrode in at a pre-determined distance from the packaging laminate. The pre-determined distance is determined by trial and error. If the distance between the packaging laminate is to far the sensitivity is too low. If the distance is to close then it may give rise to varying results. Said predefined area may be a pre-laminated hole. Hence, defects in a critical part of the packaging laminate may be detected and analysed.

The step of arranging the electrode may comprise arranging the electrode at a predetermined distance from said packaging laminate. This is advantageous in that emitted light may be utilized when detecting said defects.

The upper predetermined value of the high voltage may be between 6 and 30 kV: the predetermined distance between the electrode and the packaging material may be between 5 and 50 mm. The equipment may thus be made relatively small and readily available high power electronics may be used. The distance between the electrode and the packaging material and the high voltage value are interrelated in order to benefit from low cost equipment, i.e mounting supports and power supplies, since an increase in distance requires a corresponding increase of the voltage. The step of detecting a defect may comprise registering electrical characteristics of said dielectric breakdown, or it may comprise registering visible light. This is advantageous in that simple and cost effective equipment may be used for implementing and automating said method.

The step of detecting a defect in said packaging material may comprise registering dielectric breakdown of air, which is advantageous in that a corona discharge present at the electrode as well as at the packaging laminate may be used to detect the presence and the position of the defects.

According to a second aspect of the invention, a device for detecting defects in a packaging laminate having at least one conductive layer is provided. The device comprises a ground electrode to be connected to the conductive layer of the packaging laminate, a high voltage electrode being attached to a support for positioning the high voltage electrode adjacent to the conductive layer or at a predetermined distance from the conductive layer of the packaging laminate, and a power supply being connected to the high voltage electrode and optionally being configured to ramp the voltage from an initial value towards an upper value (both values may be predetermined), wherein said device is capable of causing dielectric breakdown between the electrode and the conductive layer of the packaging laminate upon the presence of defects in a polymer layer of said packaging laminate. The pre-determined distance can for example be 5-50 mm between the electrode and the packaging material.

The device may comprise means configured to detect a defect in said packaging material by registering said dielectrical breakdown between the electrode and the conductive layer of said packaging laminate.

Said means may be a photodetector or an oscilloscope. Preferably, said means may be an array or matrix of photodetectors thus enabling the detection of not only the presence of defects, but also the position of such.

The device may comprise a controller connected to said power supply, for controlling said power supply to ramp the voltage from an initial value to an upper value high voltage electrode. The ramping may be from an initial, optionally predetermined, value to a predetermined upper value, being separately and independent of said initial value The term dielectric breakdown should in this context be interpreted broadly so as to define a situation where a dielectric medium, such as a polymer or air, is subject to a transition from an electrically insulating state to a more electrically conductive state.

BRIEF DESCRIPTION OF THE DRAWINGS

In the following, exemplary embodiments of the invention will be described in greater detail, with reference to the enclosed drawings, in which.

DETAILED DESCRIPTION

Figure 1:
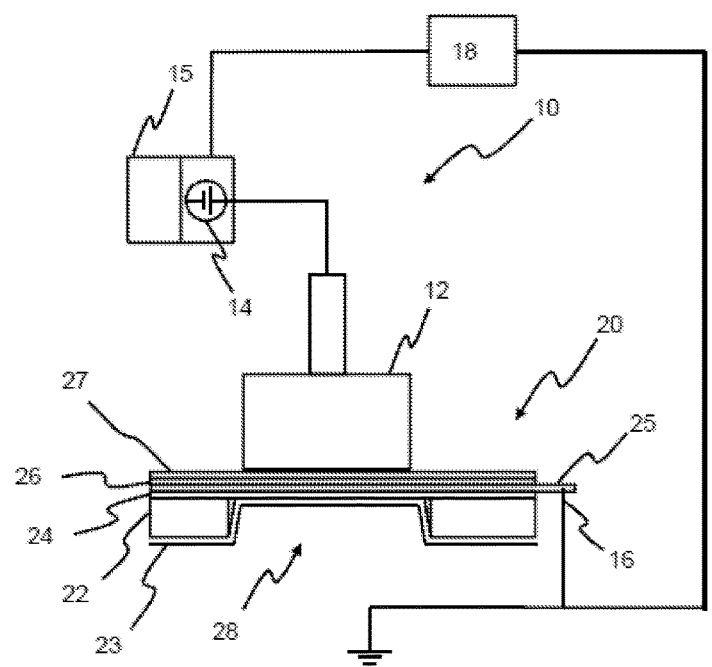
FIG. 1 is a schematic side view of a device for detecting defects in a packaging laminate according to an embodiment.

With reference to FIG. 1, a device 10 for detecting defects in a packaging laminate 20 is shown. The packaging laminate 20 has a core layer 22 of paper board which on one side is coated with a thermoplastic polymer layer 23. The inner side of the core layer 22, i.e. the side being arranged to face the product to be enclosed by said packaging laminate 20, is covered by a first polymer layer 24, a barrier film 25 of a conductive material such as aluminum, and further layers 26, 27 of polymer forming the inside of the packaging laminate 20.

The packaging laminate 20 defines a pre-laminated hole 28, which may be used later in the filling process or the package forming process for enabling the attachment of an opening device. Such pre-laminated hole may have a diameter between 20 and 50 mm. In other applications, the pre-laminated hole may e.g. be configured to receive a straw and hence the diameter is much less, e.g. between 2-15 mm such as 2, 5, and 8 mm.

The device 10 comprises an electrode 12 being electrically connected to a high voltage supply 14. Further, the device 12 comprises a contact 16 for connecting the conductive layer of the packaging laminate 20, i.e. the Al barrier film 25, to ground. A voltmeter 18 is provided in order to measure the voltage of the grounded Al foil 25.

The high voltage supply 14 is connected to a controller 15 which is configured to apply a ramped voltage to the electrode 12.

As is shown in FIG. 1, the electrode 12 is designed to fit with the pre-laminated hole 28 such that it may be arranged in close contact with the inner polymer layer 27 of the packaging laminate 20. Preferably, the diameter of the electrode 12 is slightly less than the inner diameter of the pre-laminated hole.

When the device 10 is used for detecting potential defects within the pre-laminated hole 28, the following sequence may be applied. At a first step, the electrode 12 is arranged into close contact with the inner polymer layer 27 of the pre-laminated hole 28. The grounded contact 16 is further connected to the Al barrier film 25. The controller 15 is then activated to apply a ramped voltage to the electrode 12 according to a predetermined sequence. For example, the controller is programmed to apply a linear voltage ramping from 0 to 8 kV during 2 seconds. The maximum current of the voltage generator may be set to approximately 0.02 mA.

Defects, i.e. pinholes formed within the pre-laminated hole area 28 are detected by registering dielectric breakdown, preferably by means of an oscilloscope operating as the meter 18 for detecting a voltage drop. In case no discharge has occurred when the voltage reaches 8 kV, there is no open contact between the electrode 12 and the Al foil 25 of the packaging laminate 20. Hence, the pre-laminated hole is intact without defects.

In case there are no open holes, but instead weakening zones within a polymer layer of the packaging laminate, the high voltage will eventually cause said weakening zone to burst into an open hole, thus causing an ionization being detectable by the described device. Weakening zones are parts of the packaging laminate which are thin and which may compromise the integrity of the formed package.

Figure 2A:
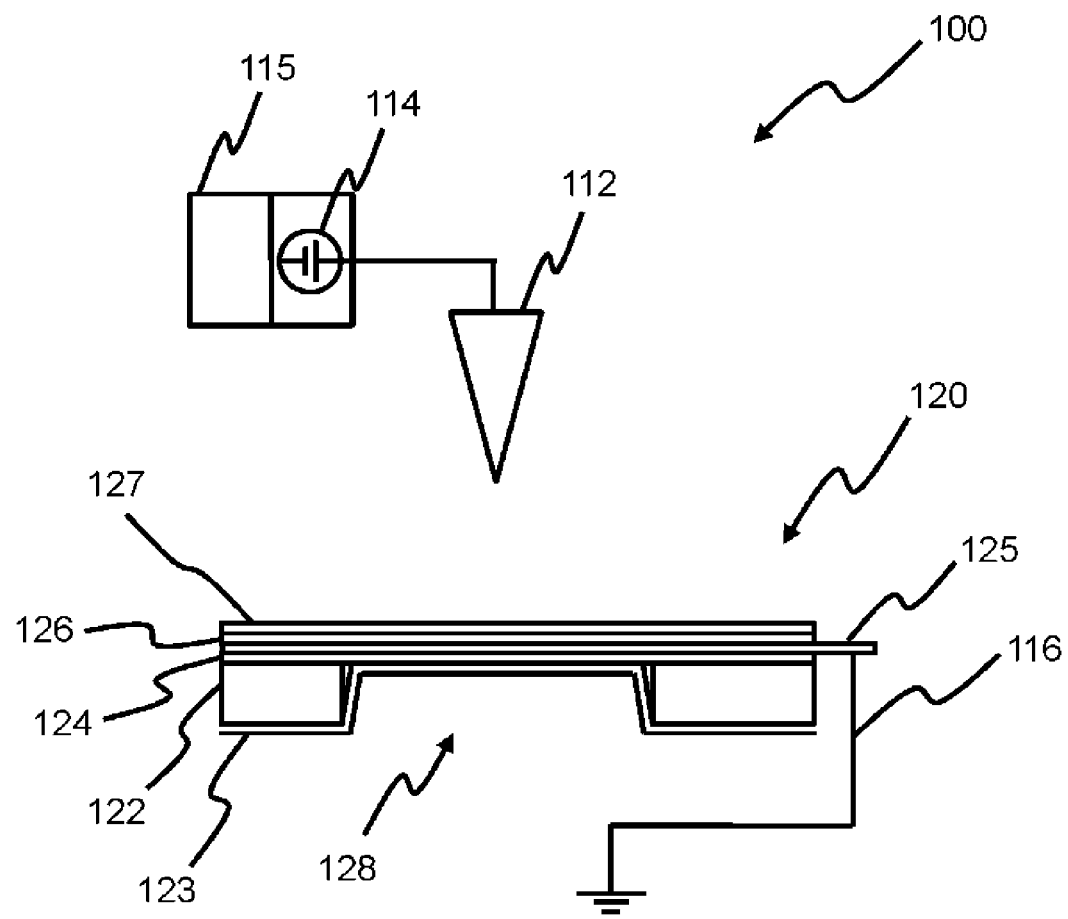
FIGS. 2a and 2b are schematic side view of a device for detecting defects in a packaging laminate according to further embodiment.

FIG. 2a discloses a device 100a for detecting defects in a packaging laminate 120 is shown. The packaging laminate 120 has a core layer 122 of paper board which on one side is coated with a thermoplastic polymer layer 123. The inner side of the core layer 122, i.e. the side being arranged to face the product to be enclosed by said packaging laminate 120, is covered by a first polymer layer 124, a barrier film 125 of a conductive material such as aluminum, and further layers 126, 127 of polymer forming the inside of the packaging laminate 120.

The packaging laminate 120 defines a pre-laminated hole 128, which may be used later in the filling process or the package forming process for enabling the attachment of an opening device. Such pre-laminated hole may have a diameter between 20 and 50 mm. In other applications, the pre-laminated hole may e.g. be configured to receive a straw and hence the diameter is much less, e.g. between 2-15 mm such as 2, 5, and 8 mm.

The device 100 comprises an electrode 112 being electrically connected to a high voltage supply 114. Further, the device 112 comprises a ground electrode 116 for connecting the conductive layer of the packaging laminate 120, i.e. the Al barrier film 125, to ground.

The high voltage supply 114 is connected to a controller 115 which is configured to regulate the high power supply 114 for applying a high voltage to the electrode 112.

The electrode 112 has a sharp tip facing the packaging laminate 120. That is, the electrode 112 has a conical shape of which the apex is directed towards the packaging laminate 120.

The electrode 112 is arranged at a distance from the packaging laminate 120, preferably by means of a rigid support (not shown). In other embodiments, the electrode 112 is arranged at a distance from the packaging laminate 120 by means of a translation stage, wherein the distance between the electrode 112 and the packaging laminate 120 may be adjusted.

The device 100a is operated according to the following principle; a defect in the form of an open hole of a polymer layer of the packaging laminate 120 will cause a small current to flow from the high voltage electrode 112 to the packaging laminate 120. When the current flows, air is partly ionized around the electrode 112 as well as at the position of the pinholes. This current may be detected either by measuring the current flowing through the circuit by means of a measuring unit (not shown), or by detecting the light emitted by said ionization, which is also known as corona discharge.

In case there are no open holes, but instead weakening zones within a polymer layer 126, 127 of the packaging laminate 120, the high voltage will eventually cause said weakening zone to burst into an open hole, thus causing an ionization being detectable by the described device.

Figure 2B:
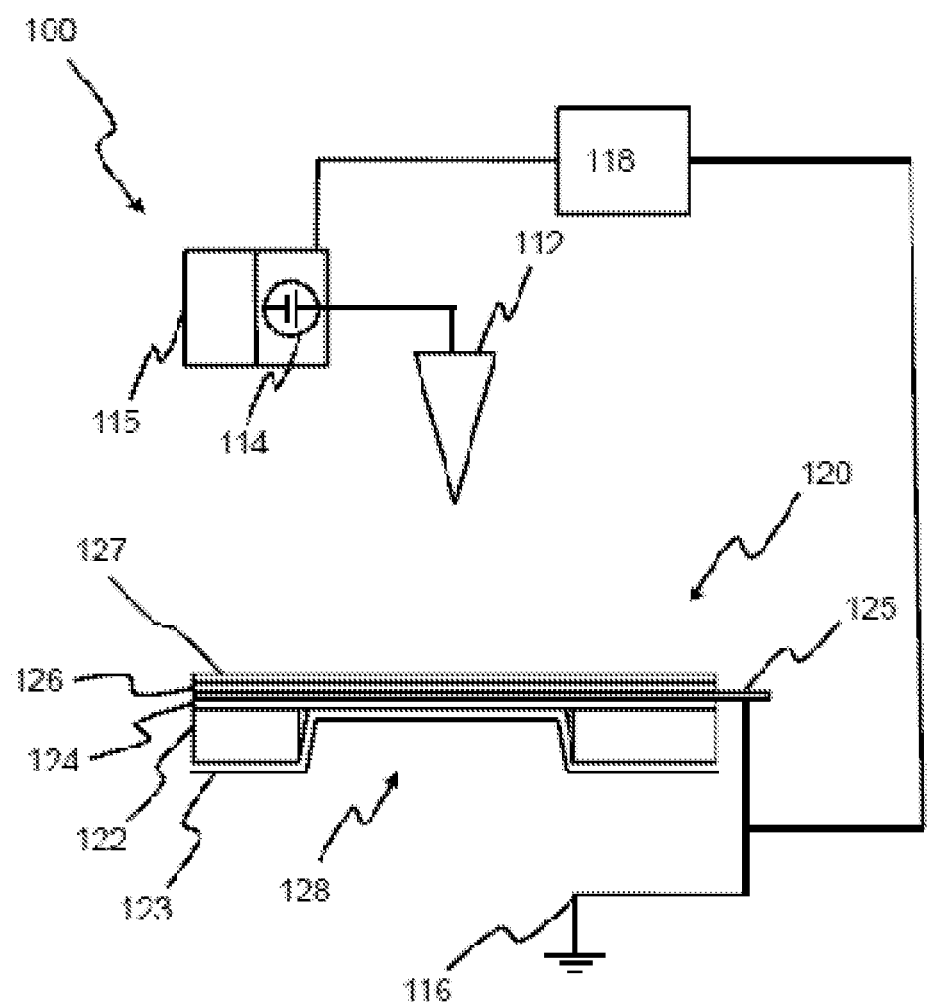

In FIG. 2b, a further embodiment of a device 100b for detecting defects in a packaging laminate 110 is shown. Here, similar to FIG. 2a, the electrode 112 has a sharp tip facing the packaging laminate 120. That is, the electrode 112 has a conical shape of which the apex is directed towards the packaging laminate 120.

The electrode 112 is arranged at a distance from the packaging laminate 120, preferably by a rigid support (not shown). Further, the device 100 includes a power supply 114 connected to the electrode 112, and a controller 115 configured to ramp the voltage supplied to the electrode 114 from the power supply 114. The aluminum foil 125 is further connected to ground via a ground electrode 116.

The device 100b is operated according to the following principle; an open hole in the packaging laminate 120 will cause a small current to flow from the electrode 112 to the packaging laminate 120. When the current flows, air is partly ionized around the electrode 112 as well as at the position of the pinholes. This current may be detected either by measuring the current flowing through the circuit by means of a measurement unit 118, or by detecting the light emitted by said ionization, which is also known as corona discharge.

In case there are no open holes, but instead weakening zones within a polymer layer 126, 127 of the packaging laminate 120, the high voltage will eventually cause said weakening zone to burst into an open hole, thus causing an ionization being detectable by the described device.

In the following, different methods for detecting defects in a pre-laminated hole of the packaging laminate will be described in more detail. The high voltage electrode is here a sharp tip, arranged at approximately 15 to 25 mm above the packaging laminate. $U_{max}$ is set to e.g. 20 kV, and $I_{max}$ is set between 0.005 and 0.1 mA.

Visual Detection, Method 1:

As a way of detecting defects, emitted light is again used. As a first step, the pre-laminated hole is aligned at a predetermined distance below the electrode, such as 15 or 22 mm. Preferably, the background light is turned off or by other means reduced. The voltage is set according to a ramped sequence, wherein the voltage is linearly increased from an initial value to an upper value, $U_{max}$. Preferably, the initial value is 0 V. In case any weakening zones are present in the packaging laminate, the high voltage will cause dielectric breakdown of the weakening zone at a specific value, and a corona discharge will be visible at the tip of the electrode. This is also the case if there are already open holes in the polymer layer of the packaging laminate. Hence, this indicates an open contact beneath the electrode. Further, each one of the open holes will glow as a result of the corona discharge. Consequently, it is possible to easily count the number of open holes of the packaging laminate at the pre-laminated hole. The described method may be further enhanced by utilizing an automatically operated detector, such as a camera or an array or matrix of photodetectors, and computer software for automatically calculating the number of open holes, as well as the position of said open holes. An algorithm for digitally reducing the impact of background light may also be used alone or in combination with the automatically operated detector for further improving the method.

Visual Detection, Method 2:

As a second way of detecting defects, emitted light is used. In a first step, the pre-laminated hole is aligned at a predetermined distance below the electrode, such as 15 or 22 mm. Preferably, the background light is turned off or by other means reduced. The voltage is set to a constant value, $U_{max}$. Preferably, $U_{max}$ may in this case be approximately 10 kV in order to detect open holes but not polymer weaknesses. In case any open holes are present in the packaging laminate, a corona discharge will be visible at the tip of the electrode. This indicates an open contact beneath the electrode. Further, each one of the open holes will glow as a result of the corona discharge. Consequently, it is possible to easily count the number of open holes of the packaging laminate at the pre-laminated hole, as well as determining the position of each open hole. As visual detection method 1 an automatically operated detector and/or an algorithm for digitally reducing the impact of background light may be used.

Oscilloscope Detection, Method 1:

In this sequence, an oscilloscope is used for monitoring the electrical characteristics of the detecting sequence. As shown in FIG. 2b, the oscilloscope 118 is connected to the power supply 114 for constantly monitoring the applied voltage. The power supply is programmed to provide a ramping sequence, such that the high voltage electrode will be subject to a voltage increasing from 0 kV to $U_{max}$ as a function of time. As a first step, the 0 kV and the $U_{max}$ levels are identified on the oscilloscope. As a second step, the pre-laminated hole is aligned at a predetermined distance below the electrode, e.g. at a distance of 22 mm. The voltage is then ramped from 0 kV towards $U_{max}$. If the trace of the oscilloscope reaches the $U_{max}$ level there are no pinholes or defects in the packaging laminate. However, in case any defects or pinholes are present in the packaging laminate the trace will bend at a voltage level below $U_{max}$. The corona discharge current is in this case in the same order of magnitude as $I_{max}$, and the electrode voltage will thus not reach the $U_{max}$ level.

Oscilloscope Detection, Method 2:

Also in this sequence, an oscilloscope is used for measuring the voltage. The power supply is programmed to provide a constant voltage $U_{max}$, e.g. 15 kV, and the packaging laminate is located away from said electrode. As a first step, the 0 kV and the $U_{max}$ levels are identified on the oscilloscope. As a second step, the voltage level on the oscilloscope reaches the $U_{max}$ level. The pre-laminated hole area of the packaging laminate is thereafter aligned at a predetermined distance below the electrode. If the trace of the oscilloscope stays at the $U_{max}$ level there are no pinholes or defects in the packaging laminate. However, in case any defects or pinholes are present in the packaging laminate the trace will bend and set at a voltage level below $U_{max}$, e.g. at 8 kV. The corona discharge formed at the defects thus reduces the voltage.

Oscilloscope Detection, Method 3

Figure 3:
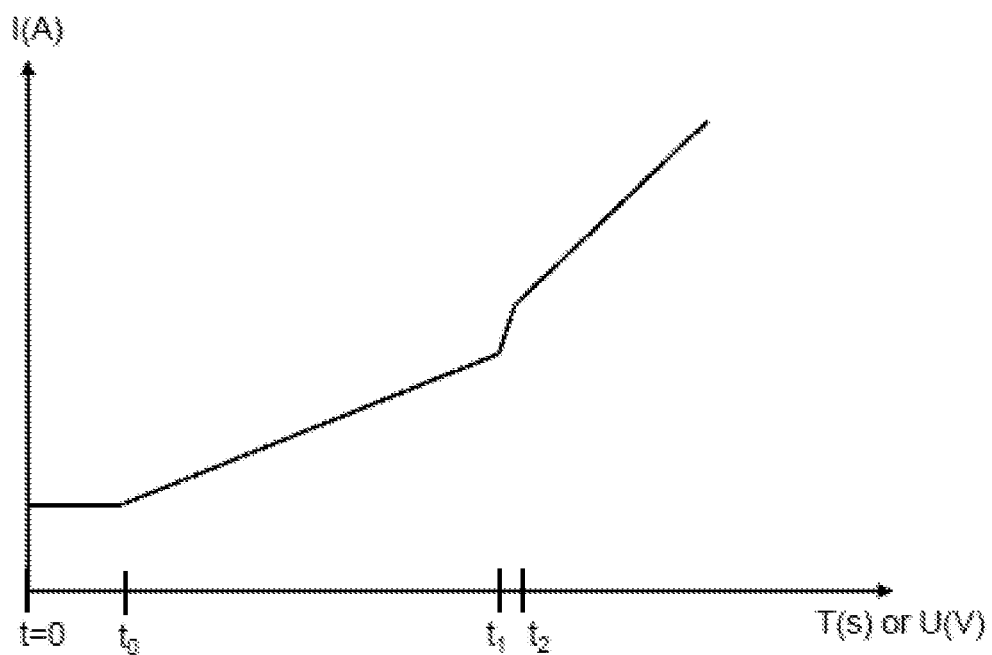
FIG. 3 is a diagram showing a current measurement sequence as a function of time.

Now turning to FIG. 2b and FIG. 3, a measurement sequence of the current flowing through the circuit is shown. For performing this sequence the oscilloscope is connected to the power supply for monitoring the applied voltage, and one probe of the oscilloscope is further connected to the conductive layer of the packaging laminate in order to measure the current flowing to ground. The setup is shown in FIG. 2b. Here, the oscilloscope 118 is connected to the power supply 114 as well as to the ground electrode 116. Starting at $t=0$, the applied voltage will allow a certain current to flow through the circuit. As the voltage is increased, the current will be almost constant until a specific time $t_0$. At this point, the high voltage between the electrode and the conductive layer of the packaging laminate has caused an open hole in the inner multilayer polymer film. The electrical conductivity is thus increased, and the current flowing through the circuit will be increased due to increased voltage. At $t_1$, dielectric breakdown will cause another defect or weakening zone to break and there will thus be a rapid increase of the current flowing through the circuit. At $t_2$, the current derivative will decrease to a constant value being less than the derivative between $t_1$ and $t_2$, but being greater than the derivative taken between $t_0$ and $t_1$. Hence, it is possible to determine the number of defects of the sample by analyzing the current curve during voltage ramping. If several defects are present, the current curve will indicate this by the provision of several subsequent step-like increments of the current.

Figure 4A:
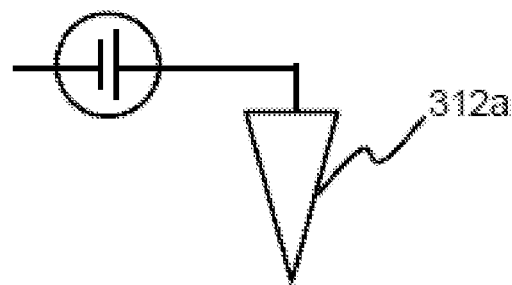
FIGS. 4a, 4b, and 4c are schematic side views of an electrode for use with a device for detecting defects in a packaging laminate.
Figure 4B:
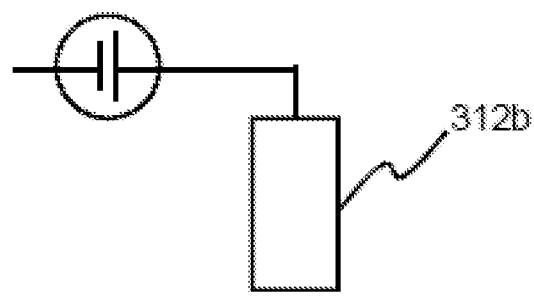
Figure 4C:
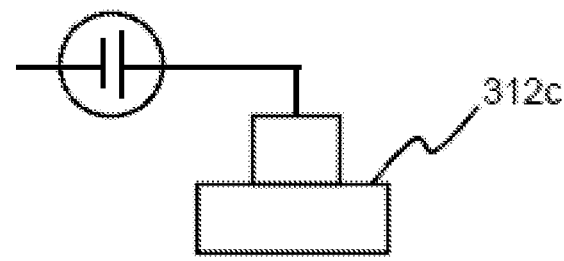

With reference to FIGS. 4a to 4c, different embodiments of an electrode for use in a method for detecting defects in a packaging laminate are shown. Starting with FIG. 4a, the electrode 312a has a conical shape, i.e. the apex of the electrode 312a is directed towards the packaging laminate to be analyzed. In FIG. 4b, the electrode 312b has a cylindrical shape, thus allowing the pre-laminated hole of the packaging laminate to be analyzed in close contact by sequential moving of the electrode relative the position of the pre-laminated hole. Further, in FIG. 4c the electrode has a cylindrical shape being substantially greater than the dimensions of the electrode shown in FIG. 4b, to be arranged in close contact with the entire area of the pre-laminated hole as has been described previously with reference to FIG. 1. Hence, the electrode 312a is preferred when the electrode is arranged at a distance from the sample to be analyzed. The electrode 312b may be preferred if the sample is to be analyzed in close contact sequentially, which may be the case if different areas of the sample should be analyzed individually. The electrode 312c is consequently preferred if the entire sample is to be analyzed in close contact by one solitary measurement sequence.

Again returning to FIG. 1, the electrode 12 is designed to fit with the pre-laminated hole 28 such that it may be arranged in close contact with the inner polymer layer 27 of the packaging laminate 20. Preferably, the diameter of the electrode 12 is slightly less than the inner diameter of the pre-laminated hole. Of course, an electrode according to FIG. 4b may also be used, thereby allowing the pre-laminated hole area to be swept by said electrode 312b.

When the device 10 is used for detecting potential defects within the pre-laminated hole 28, the following sequence may be applied. At a first step, the electrode 12 is arranged into close contact with the polymer layer 27 of the pre-laminated hole 28. The grounded electrode 16 is further connected to the Al barrier film 25. The controller 15 is then activated to apply a ramped voltage to the electrode 12 according to a predetermined sequence. For example, the controller is programmed to apply a linear voltage ramping from 0 to 10 kV during 10 seconds. The maximum current of the voltage generator may be set to approximately 0.02 mA.

Defects, i.e. weakening zones within a polymer layer of the packaging laminate formed within the pre-laminated hole area 28 are detected by registering dielectric breakdown of the polymer layer, preferably by means of the oscilloscope operating as the meter 18 for detecting a voltage drop in accordance with the previously described oscilloscope detection, method 1. In case no discharge has occurred when the voltage reaches 10 kV, there are no weakening zones between the electrode 12 and the Al foil 25 of the packaging laminate 20. Hence, the pre-laminated hole is intact without defects. However, if there is a detected voltage drop during the ramping, the sequence may be interrupted. Following this, the electrode is raised to approximately 2 to 5 mm above the packaging laminate, and a high voltage is again applied. In accordance with the previously described methods for visual detection, a light emission at the position of the open hole will clearly indicate the position of the defect.

According to a yet further embodiment, a method for measuring the thickness of a polymer layer in a packaging laminate will be described. The method is implemented by means of a device as shown in FIG. 1, i.e. a device wherein the electrode is arranged in close contact with the surface of the pre-laminated hole. During tracing of the ramped electrode voltage, the measured voltage curve will reach a peak and then drop to a base line level when the discharge has punched a hole in the packaging laminate. Typically, the base line voltage may vary between 1 and 2 kV. This voltage corresponds to the open contact of the packaging laminate. For example, if the open contact is located at the edge of the pre-laminated hole area, the base line level is generally lower since the distance between the electrode and the Al foil is smaller. On the other hand, if the open contact is found to be inside the pre-laminated hole area, there might be a small air gap added to the distance and consequently, the base line voltage is higher.

From test results performed by the inventors, the following measurements have been observed relating to the thickness of the polymeric layer arranged on the Al foil, i.e. the layer 27 shown in FIG. 1.

| Discharge voltage range | Polymer layer thickness |
| --- | --- |
| 0-2 kV | open pinhole or very thin film |
| 2-5 kV | up to 0.005 mm |
| 5-8 kV | 0.005-0.01 mm |
| above 8 kV | above 0.01 mm |

The above measurements were made on a packaging laminate wherein the polymer layer 27 is made of PE. However, the above mentioned method for determining the thickness may also be implemented for determining thicknesses of other polymeric materials within a packaging laminate.

The device according to FIG. 1 may be used in combination with the device shown in FIG. 2a or FIG. 2b for detecting and analyzing defects in a packaging laminate. In this method, two different devices are used, namely the one shown in FIG. 1 as well as the device shown in FIG. 2b.

As a first step, a sharp tip electrode is placed above the pre-laminated hole area of a packaging laminate, in accordance with the configuration shown in FIG. 2b. However, the controller 115 is here operated to apply a constant high voltage, e.g. in the order of 10 kV. If a pinhole or defect is present in the pre-laminated hole area, a corona discharge will cause violet light to indicate the position of said defect. If several defects are present, the corona discharge will occur at all defects simultaneously. As an alternative, electrical measurements may also indicate the presence of defects in the packaging laminate.

As a second step, a plate electrode of the same size as the pre-laminated hole area is positioned in close contact with the pre-laminated hole. This setup is similar to what is shown in FIG. 1. The voltage is then ramped from 0 kV to e.g. 10 kV and the weakest defect, i.e. the position where dielectric breakdown is first to occur, will break at a specific voltage. The voltage value is registered, as well as the base line level after break down. From those two different values, the thickness of the polymeric layer may be determined.

It is readily understood that all references to above/below are merely for illustrative purposes, without any limiting effect on the scope of protection. Moreover, it should be realized that equivalent setups to those described may include setups having a fixed high voltage electrode while having a moveable packaging laminate.

In the claims, the term "comprises/comprising" does not exclude the presence of other elements or steps. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second" etc do not preclude a plurality. Reference signs in the claims are provided merely as a clarifying example and shall not be construed as limiting the scope of the claims in any way.

The invention claimed is:

1. A method for detecting defects in a packaging laminate, comprising:
   providing the packaging laminate having at least one conductive layer, a base paperboard layer, and a polymer layer having a weakening zone;
   grounding the conductive layer of the packaging laminate,
   arranging an electrode in relation to the packaging laminate,
   applying a voltage to the electrode by ramping the voltage from an initial value towards an upper predetermined value, wherein the voltage applied is sufficiently high to cause the weakening zone in the polymer layer of the packaging laminate to burst into an open hole in the packaging laminate,
   detecting the weakening zone in the polymer layer of the packaging laminate by registering dielectric breakdown between the electrode and the conductive layer of the packaging laminate,
   using an oscilloscope for registering the dielectric breakdown, wherein one probe of the oscilloscope is connected to the conductive layer of the packaging laminate in order to measure current flowing to the ground of the conductive layer, and
   determining the number of defects in the packaging laminate by analyzing a curve of the measured current during the ramping of the voltage, wherein step-like increments in the current curve are indicative of the number of defects.

2. The method according to claim 1, wherein the step of arranging the electrode in relation to the packaging laminate comprises bringing the electrode in close contact with a predefined area of the packaging laminate.

3. The method according to claim 2, wherein the predefined area is a pre-laminated hole.

4. The method according to claim 1, wherein the step of arranging the electrode in relation to the packaging laminate comprises arranging the electrode at a predetermined distance from the packaging laminate.

5. The method according to claim 4, wherein the predetermined distance between the electrode and the packaging material is between 5 and 50 mm.

6. The method according to claim 1, wherein the upper predetermined value of the high voltage is between 1.5 and 30 kV.

7. The method according to claim 1, wherein the step of detecting the weakening zone comprises registering electrical characteristics of the dielectric breakdown.

8. The method according to claim 1, wherein the step of detecting the weakening zone comprises at least one of registering visible light, or registering dielectric breakdown of air.

9. A device configured to detect defects in a packaging laminate, comprising:
   a ground electrode to be connected to the conductive layer of the packaging laminate, the packaging laminate having at least one conductive layer and a base paperboard layer,
   an electrode being attached to a support for positioning the electrode adjacent to the conductive layer of the packaging laminate, or keeping the electrode at a predetermined distance from the conductive layer of the packaging laminate, a power supply being connected to the electrode and being configured to ramp the voltage from an initial value towards an upper predetermined value, wherein the device is capable of causing dielectric breakdown between the electrode and the conductive layer of the packaging laminate upon the presence of weakening zones in a polymer layer of the packaging laminate, and wherein the device is configured to apply a voltage sufficiently high to cause the weakening zones to burst into open holes in the polymer layer of the packaging laminate, and an oscilloscope configured to register the dielectric breakdown, wherein one probe of the oscilloscope is connected to the conductive layer of the packaging laminate in order to measure a current flowing to the ground electrode, and wherein the device is configured to determine the number of defects in the packaging laminate by analyzing a curve of the measured current during the ramping of the voltage, wherein step-like increments in the current curve are indicative of the number of defects.

10. The device according to claim 9, further comprising a controller connected to the power supply for controlling the power supply to apply a ramped voltage to the electrode.

11. The device according to claim 9, further comprising means configured to detect a defect in the packaging laminate by registering the dielectrical breakdown between the electrode and the conductive layer of the packaging laminate.

12. The device according to claim 11, wherein the means configured to detect a defect is an optical device.

13. The device according to claim 11, wherein the means configured to detect a defect is an electric sensor.

14. The method according to claim 1, wherein the ramping of the voltage is according to a predetermined sequence.

15. The method according to claim 1, wherein the weakening zone does not include an open hole.

16. The device according to claim 9, wherein the weakening zone does not include an open hole.

* * * * *